(12) United States Patent
Duret et al.

(10) Patent No.: US 7,354,269 B2
(45) Date of Patent: Apr. 8, 2008

(54) ELECTRO-OPTICAL DEVICE FOR THE PHOTO-POLYMERIZATION OF COMPOSITE MATERIAL

(75) Inventors: François Duret, Fleury d'Aude (FR); Hervé Noui, Salles d'Aude (FR); Jean-Michel Decaudin, Velaux (FR)

(73) Assignee: Satelec- Societe Pourlla-Conception des Applications des Techniques Electroniques, Merignac (FR)

( * ) Notice: Subject to any disclaimer, the term of this patent is extended or adjusted under 35 U.S.C. 154(b) by 0 days.

(21) Appl. No.: 10/502,889

(22) PCT Filed: Jan. 30, 2002

(86) PCT No.: PCT/FR02/00354

§ 371 (c)(1), (2), (4) Date: Jan. 18, 2005

(87) PCT Pub. No.: WO03/068102

PCT Pub. Date: Aug. 21, 2003

(65) Prior Publication Data

US 2005/0123877 A1 Jun. 9, 2005

(51) Int. Cl.
*A61C 3/00* (2006.01)
(52) U.S. Cl. ........................................................ 433/29
(58) Field of Classification Search ................. 433/29, 433/31, 32, 215; 362/119, 800, 802
See application file for complete search history.

(56) References Cited

U.S. PATENT DOCUMENTS

| 4,793,807 | A | * | 12/1988 | Friedman et al. | ............. | 433/80 |
| 5,476,379 | A | * | 12/1995 | Disel | ............................ | 433/29 |
| 6,159,005 | A | * | 12/2000 | Herold et al. | .................. | 433/29 |
| 6,200,134 | B1 | * | 3/2001 | Kovac et al. | .................. | 433/29 |
| 6,203,191 | B1 | * | 3/2001 | Mongan | ....................... | 374/43 |
| 6,312,254 | B1 | * | 11/2001 | Friedman | ..................... | 433/32 |
| 6,331,111 | B1 | * | 12/2001 | Cao | ............... | 433/29 |
| 6,611,110 | B1 | * | 8/2003 | Fregoso | ...................... | 315/224 |
| 2001/0016652 | A1 | | 8/2001 | Manoharan et al. | | |
| 2001/0033503 | A1 | * | 10/2001 | Hamp et al. | .................. | 363/73 |
| 2001/0046652 | A1 | * | 11/2001 | Ostler et al. | .................. | 433/29 |

FOREIGN PATENT DOCUMENTS

WO  01/60280  8/2001

* cited by examiner

Primary Examiner—Cary E. O'Connor
(74) Attorney, Agent, or Firm—Young & Thompson

(57) ABSTRACT

The invention relates to an electro-optical device for the photo-polymerization of composite material, and is used in particular in the dental field. The inventive device comprises a light source (2) which is defined by an LED or a group of LEDs. It comprises electrical power supply means consisting of a battery (4) which is associated with a direct current/direct current converter device (7) commonly known as a DC/DC converter, passive means (3) for the evacuation of heat, and a central management unit (5) for operating parameters of the light source for the definition of a determined photo-polymerization energy profile.

18 Claims, 4 Drawing Sheets

ELECTRO-OPTICAL DEVICE FOR THE PHOTO-POLYMERIZATION OF COMPOSITE MATERIAL

The present invention has for its object an electro-optical device for the photo-polymerization of composite materials, particularly applicable in the dental field.

The composite materials used in the dental art are generally based on a photo-polymerizable resin of which the molecular structure is transformed under the effect of a light radiation of a given wavelength as a function of the capacity of absorption of the material used. In this way, during polymerization, this radiation activates the photo initiators of the material for an exposure time calculated as a function of the energy of this radiation in order to avoid too great an overheating of the tissues surrounding the zone of treatment.

It should be observed that the parameters of the radiation, wavelength, intensity, exposure time, depend, of course, on the particular composition of each composite, but also on its colour and its thickness. A darker composite of greater mass will necessitate for its photo-polymerization a radiation of greater intensity. This is what is called the parameters of polymerization. In order to allow these factors to act in optimal manner, i.e. in manner invariable during the exposure time and for a time sufficiently long for a practitioner to be able to use them during his sessions of care without dangerous interruption, no sufficiently reliable solution has been proposed.

Photo-polymerization devices responding to the description which has been made hereinbefore are already known, which use electro-luminescent diodes, usually called LEDs, capable of emitting, often, a radiation of wave-lengths included between 380 and 510 nm. For example, such devices comprise a power card, a cooling system, a source of light and optical means for orienting and emitting the light energy produced by said source in the direction of the zone to be illuminated (or clinical site). These electronic means are for example in the form of a supply card, of the type with supply by linear regulation, the current of the LEDs being defined by polarization resistance, and of an active ventilation system (ventilator or by Peltier effect) or a passive one (ceramic card).

In the end, these heretofore known apparatus are adapted to emit a radiation of a defined profile without possibility for the operator to be certain that its power is stable and obliging him to support the noxious effects of the cooling ventilator or the debatable efficiency of the passive cooling systems mentioned above. In fact, the only parameter on which an action is possible with precision is the time of illumination. Such devices thus hardly present any guarantee of use and are of limited application.

As light source in this type of apparatus, use is made, for example, of mercury vapour lamps which present the drawback of emitting in the ultra-violet spectrum, which is dangerous for the patients' eyes and buccal mucous membrane. Such lamps use sources of supply requiring high starting currents and voltages, and cooling systems most often based on ventilators and therefore with pulsed air or possibly, for the most powerful ones, based on water circulation and radiators. Other devices use halogen lamps which have the drawback of presenting a low lumen/watt ratio and a high heat dissipation with respect to the light energy produced, this making it necessary to limit the rise of the power in order to obtain greater intensities. Such lamps use supply sources whose yield is without comparison with respect to the useful power, and cooling systems likewise based on pulsed air.

Other devices are equipped with lasers, but the light beams that they generate correspond to a monochromatic light which, due to its reduced wavelength spectrum, can, there again, polymerize only well defined composites. Such lamps use complex supply sources and cooling systems with pulsed air or circulation of water. Moreover, the lasers are expensive apparatus which, in addition, present high maintenance and implementation costs.

Devices are also known which employ spaced electrodes subjected to differences in electrical potential adapted to produce an electric arc through a partially ionized gas at high temperature. Such systems employ, in combination, an infrared filter placed immediately in front of the source and allowing a light spectrum of emission included between 400 and 800 nm to be obtained. A low-pass filter makes it possible then to fix the high cut-off frequency of the filter at about 515 nm. Such lamps use supply sources requiring starting voltages of several kilovolts and cooling systems employing pulsed air for the less powerful and circulation of water for the others.

However, in these devices, the filtering system does not make it possible to increase, without danger, the light power of the source, as the light energy absorbed by the biological tissues may lead to their destruction in the case of considerable rise in temperature. In addition, the energy profile, which represents the variations of the light intensity emitted in the course of time, cannot be modified.

This consequently excludes any possibility of adapting it to composite materials of different colours, for example.

Photo-polymerizing devices also exist, which use plasma energy and have an isolated selective emission zone thanks to more or less complex filtrations. A document FR-98 01243 describes such an apparatus. Such lamps use supply sources which, there again, necessitate starting voltages of several kilovolts and cooling systems employing pulsed air or circulation of water.

It should be noted that such devices present the particularity of allowing highly caloric radiations to pass in zones beyond the 1200 nm. This has the consequence of dangerously raising the temperature at the moment of polymerization. Furthermore, such devices require high-performance cooling systems which are of high cost and weight.

Photo-polymerization devices are also known, for example by documents EP-A-0 880 945, JP-A-9010238, U.S. Pat. No. 5,634,711, PCT/AU97/00207, of which the light source is defined by LEDs. In fact, it is question of a plurality of blue LEDs disposed on a support deck perpendicularly to the interior of the body of the apparatus. At the front of this deck of LED diodes are located means for concentrating the radiations emitted and for orienting them in the direction of a wage guide of which the distal end projects this concentrated radiation on the surface to be treated. This device may take the shape of a gun connected to an outside electrical energy supply. These lamps use as supply sources resistors for determining the polarization current of the LEDs. Contrarily to the devices described previously, the need for cooling is less. In effect, the conversion "electrical energy" into "light energy" is effected with a very good yield and when the LEDs are used at their nominal characteristic, the heat dissipation generally does not necessitate active cooling means. In the case of use with photo-polymerization, it is sought to obtain the greatest power of the diodes, this being possible by causing them to function with a current greater than that normally provided.

If no precaution is taken, this increase of the current generates an overheating of the diodes which modifies their electrical characteristics, and a lowering of the power emitted. In that case, the result inverse to that desired is obtained. The common mastery of the thermal behaviour and of the electrical supply are necessary to obtain the highest power.

In all the cases cited, and more particularly those relating to the LED sources, the apparatus receives conventional supply systems which are unstable in time, and the general behaviour is very sensitive to the rise in temperature. The manufacturers of LEDs have noted in particular that a rise in temperature of 40° may bring about a modification of the current transmitted and therefore a lowering of power of close to 50%.

All the assemblies which have been proposed solve the problem only partially or oblige the user to use conventional cooling systems which are noisy and have to be connected to the mains, thus considerably limiting his freedom to work. Moreover, it in no way solves the problem raised, insofar as it is hardly possible to modify the intensity of this radiation, its density per surface unit or the number of sequences of irradiation, for all that. Finally, the application of the apparatus described in these documents is, there again, limited to a determined time, the operator having only the possibility of managing, to a lesser extent, the time of illumination and of recharging the batteries in order to be sure that he is respecting and guaranteeing the thickness of the material to be photo-polymerized.

In the end, although it is possible, through the known techniques, to play on the exposure in primary manner, i.e. to reduce or increase the exposure time, it is impossible, in real time today, to do so with a large time or power scale. In effect, no dynamic variation is possible with the present-day apparatus.

The present invention has for its object to overcome the afore-mentioned drawbacks by proposing an electro-optical device for the photo-polymerization of composite materials, applicable in particular in the dental domain allowing an independent, stable and adjustable supply of energy, comprising an optimized and stable electronic system, a light source based on LED not requiring active ventilation, as well as thermal means for orienting and evacuating the heat energy produced by said source in order to ensure a reliable polymerization during the clinical act and in time.

Thus the invention concerns an electro-optical device for the photo-polymerization of composite materials, applicable in particular in the dental field, of the type comprising a light source which is defined by an LED or a group of LEDs, and which is essentially characterized in that it comprises electronic power supply means consisting of a battery which is associated with a direct current/direct current converter device, commonly known as a DC/DC converter, passive means for the evacuation of heat, as well as a central management unit for the operating parameters of the light source for the definition of a determined photo-polymerization energy profile.

The DC/DC converter, of which the output is variable, makes it possible to adjust without resistance the polarization current by limitation of the direct voltage, with the result that this makes it possible to securitize the quality of the care given thanks to a stability of the power emitted by monitoring the heat behaviour, a long life of the battery, several days, thanks to a reduced consumption of electricity, the maintenance of the power emitted whatever the state of charge of the battery, up to complete discharge of the latter.

According to an additional characteristic of the device according to the invention, it comprises a power circuit making it possible to supply each LED or LED group at a predefined value by cyclic ratio modulation.

According to another additional characteristic of the device according to the invention, it comprises a device for correcting the thermal drift of the LEDs.

According to another additional characteristic of the device according to the invention, the passive heat evacuation means comprises an LED supporting electronic card whose design includes metallic tracks for transfer of the heat from the base of each of the LEDs towards the periphery of the card.

According to another additional characteristic of the device according to the invention, the passive heat evacuation means comprise a heat-conducting material disposed around the casing of each of the LEDs in order to remove the maximum of calories from each of the diodes and to transfer them to the periphery of the card.

According to another additional characteristic of the device according to the invention, the passive heat evacuation means comprise a metallic radiator connected to the card by a heat-transmission paste or glue, and a thermal joint between said card and said radiator towards a metal piece with high thermal inertia serving as receptacle for calories and as support for the optical assemblies necessary for the system.

According to another additional characteristic of the device according to the invention, the passive heat evacuation means comprise a temperature sensor embedded in the thermal joint and making it possible to have, in real time, the temperature level of the optical assembly.

The optical systems necessary for conducting the light so as to maintain the power emitted in respect of the energy needs for photo-polymerization as a function of the characteristics of the composite material to be photo-polymerized.

According to a particular form of embodiment of the device according to the invention, the heat evacuation means comprise one or the other of the following characteristics, individually or in combination:

an electronic card on which the LEDs are welded, the welding spots being connected to electrical tracks of large dimension having a very good heat conductivity, said electronic card is pierced with metallized thermal wells which conduct the calories as rapidly as possible towards the rear face of the card and therefore far from the LEDs.

heat-conducting products placed in contact with the peripheral walls of the diodes which are not in contact with the card itself. These products may be pasty and deposited between the diodes then hardened thereafter, they may equally well be solid and cut to the exact shape of the location of the diodes maintained intimately with the diodes by means of a good heat conductor (paste or glue).

a metallic radiator at the rear of the card, connected to said card by a paste or thermal glue, serving to recover the calories coming from the thermal wells traversing the card.

the elements are thermally connected by paste or thermal glue to a metallic piece of high thermal inertia which also serves as support for the optical elements. This latter piece serves to pump the calories rapidly and to store them temporarily when the lamp is lit and restores them more slowly by conduction or convection towards the assembly of the system when the lamp is not used.

a temperature detection system allowing the supply to be cut when the storage capacity of the metallic piece is attained. According to an additional characteristic of the device according to the invention, the electronic supply means comprise:

a circuit for control by shift register and cyclic ratio modulation making it possible to select and modulate the power of emission of each LED group, a high-yield DC/DC converter supplying the control circuit by lowering the battery voltage, a direct polarization of the electro-luminescent diodes by the output of the DC/DC converter by using the internal resistance of the diodes, a system for adjusting said polarization voltage in order to vary the supply current of the diodes and consequently the optical power, an automatic correction of this polarization voltage by thermal servo-control in order to have available a constant output power.

The high-yield DC/DC converter makes it possible to reduce the primary current issuing from the battery thus prolonging its life duration and its autonomy. Moreover, the use of this DC/DC converter makes it possible to dispense with the variations of voltages due to the variations of the level of charge of the battery.

The light source advantageously comprises a means for measuring the temperature adapted to detect the maximum storage of temperature compatible with the stability of optical power emitted.

This monitoring system advantageously functions between two minimum and maximum levels functioning in hysteresis in order to limit the current in the diodes in the event of dysfunction of the heat regulation system and thus reduce overheating.

The battery is preferably of the Li ion battery type provided with a temperature sensor in order to securitize the apparatus.

The battery is advantageously of the hybrid Ion battery type making it possible to manage the charge level and to display it on an LCD screen.

From among the means for maintaining the power of the card, it will be observed that the device for monitoring and stabilizing the power is piloted by servo-control, this enabling this power to be maintained at the desired value.

The present invention advantageously comprises a potentiometer for preadjusting the power setting, this making it possible to adjust an industrial production to the same known value thanks to an individual adjustment of each apparatus.

Of course, such a solution enables other functionalities to be envisaged, such as remote adjustment, tele-diagnosis or remote maintenance of the power of the photo-polymerization device according to the invention, or the remote adjustment via Internet, or the adjustment by the user or the upgrading of the power in after sales service.

The advantages arising out of the present invention consist in that the device is applicable virtually universally, as its use is not simply limited to a determined type of LED lamp. Insofar as it is possible to adopt any photo-polymerization energy profile, this device is, in fact, capable of being adapted to the particularities of each of these lamps. The operator is therefore no longer obliged to use a particular LED range to polymerize the composite materials, apart from the fact that he can modify the operating conditions of his photo-polymerization device himself by taking into account his own experience, but also the conditions of use of the material. Finally, a correct adjustment of the power and its thermal monitoring enables the needs expressed in this domain to be answered.

Other objects and advantages of the present invention will appear in the following description which relates to a form of embodiment given by way of indicative and non-limiting example.

Understanding of this description will be facilitated by studying the accompanying drawings, in which:

FIG. 1 schematically shows the device forming the subject matter of the present invention, its body appearing in transparency.

FIG. 2 schematically shows LED diode supporting discs oriented perpendicularly to the longitudinal axis of the body of the device and distributed about this axis.

FIG. 3 schematically shows FIG. 2 in transverse section.

FIG. 4 schematically shows the device and an electrical charging support adapted thereto.

FIG. 5 corresponds to a schematic representation of the device including the part defining the power supply and the means employed.

FIG. 6 is a view similar to FIG. 5, where the systems of adjustment appear.

FIG. 7 schematically illustrates the device forming the subject matter of the invention, equipped with means for remote acquisition, of the energy type and/or other data in its memory.

As is shown in these Figures, the present invention relates to a device 1 for photo-polymerization of composite materials which will find more particular interest in the dental domain.

This device 1 comprises a body 10 inside which its principal constituent elements are positioned. Thus, this device 1 comprises a light source 2 in the form of an optical cone and preferably comprising electro-luminescent diodes 20, called LEDs, capable of emitting a light radiation of a determined wave length or in a defined wave length spectrum.

Figure 2:
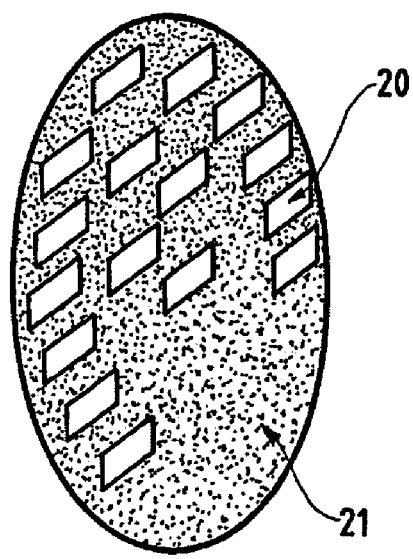
Figure 3:
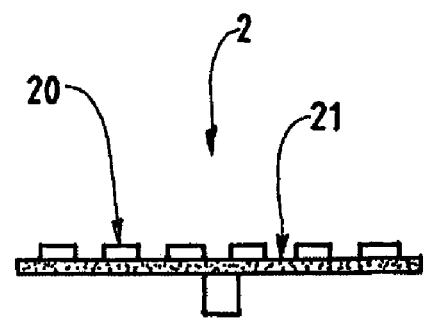

By way of example shown in FIGS. 2 and 3, the LED diodes 20 are distributed on a support disc 21 extending perpendicularly to the longitudinal axis of the body 10.

The device 1 also comprises heat evacuation means 3 for orienting and emitting the heat energy produced by the light source 2 in the direction of a zone corresponding to an evacuation which does not reduce the efficiency of the device.

Figure 1:
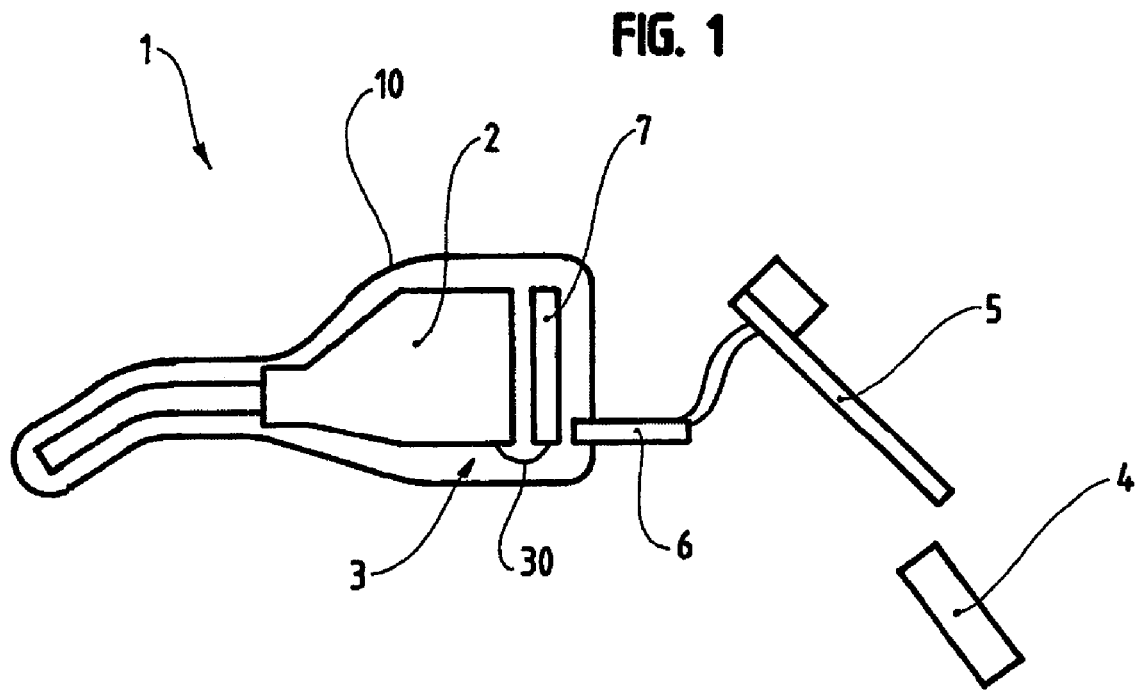

As visible in this FIG. 1, such heat evacuation means 3 may be constituted by a heat evacuation guide 30 located in the front part of the body 10.

It will be observed more particularly that the present invention is in no way limited to such thermal or opto-electronic means. In effect, they may also take the form of one or more evacuation channels, even that of a paste, known by the person skilled in the art familiar with the domain of heat guides and which, in the present application, presents the advantage of promoting the conduction of the calories generated, and therefore making it possible to conserve the same power emitted. Insofar as one of the particularities of the present invention consists in optimizing the reaction of photo-polymerization, this reduction of the energy drop of the light emission is very important.

In addition, these heat evacuation means 3 may be in the form of a track, each track being in register with a LED 20, this allowing a heat evacuation for each of the LEDs 20 in selective manner on the support. The device is thus transformed into a controllable and individual elimination means. As has already been set forth hereinabove, this particularity allows a controllable optimization of the heat evacuation.

Furthermore, the source of energy 4, which consists in FIG. 1 in a battery, and the optical means may be integrated in an interchangeable part of the body 10, thanks to appropriate connection means, this facilitating replacement thereof in the case of ageing of the light source 2, without counting the fact that the latter may be substituted by a more or less powerful energy source, for example comprising more or fewer LED diodes 20. In addition, the removability of the energy source 4 makes it possible to replace the latter rapidly in order to replace it in the event of failure.

The device further comprises a central unit 5 for managing the operation of the light source 2 for the definition of a determined photo-polymerization energy profile.

Figure 4:
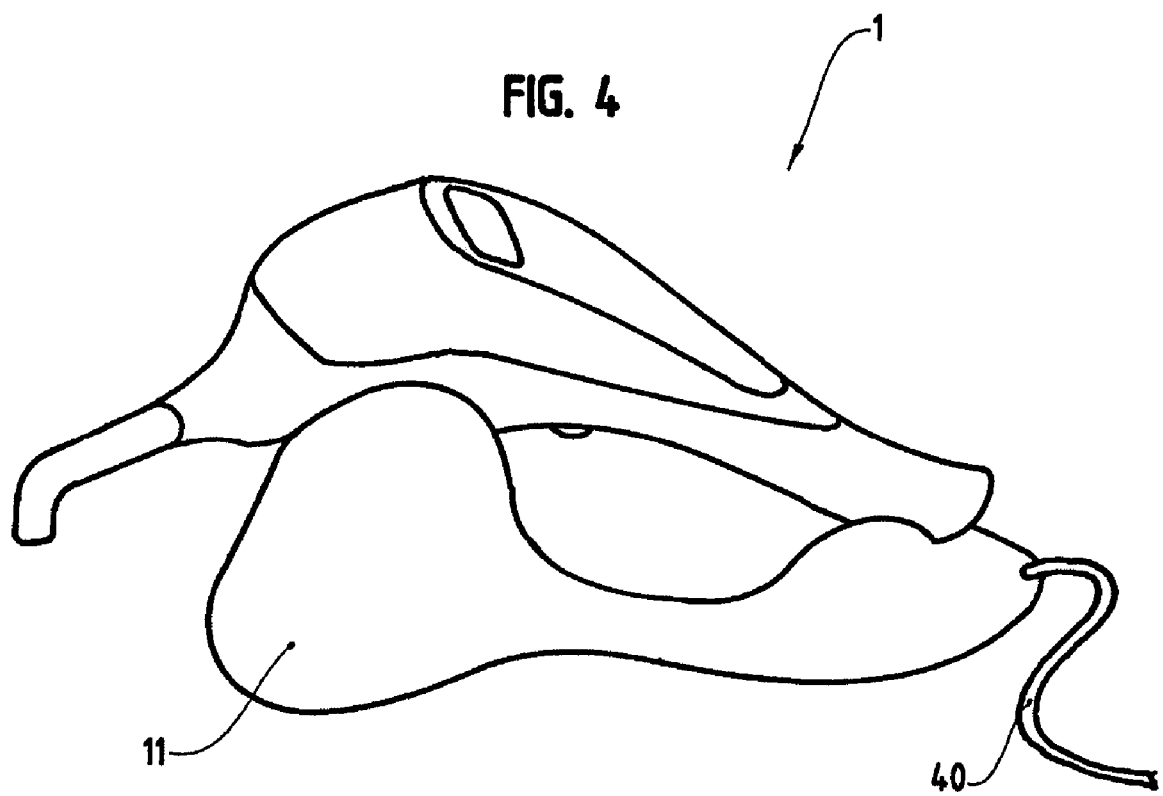

In this way, thanks to an autonomous electrical supply, therefore one or more batteries 4, preferably of the rechargeable type and/or means 40 for connection to the mains supplying electricity to a dwelling, shown in FIG. 4, the central unit 5 controls, via a power card 6, the operation of the light source 2 in determined sequences of illumination and with defined powers.

In FIG. 4, a charging support 11 has been shown which is more particularly adapted to receive the device 1 in the course of recharging of the batteries 4 integrated in the latter.

Figure 8:
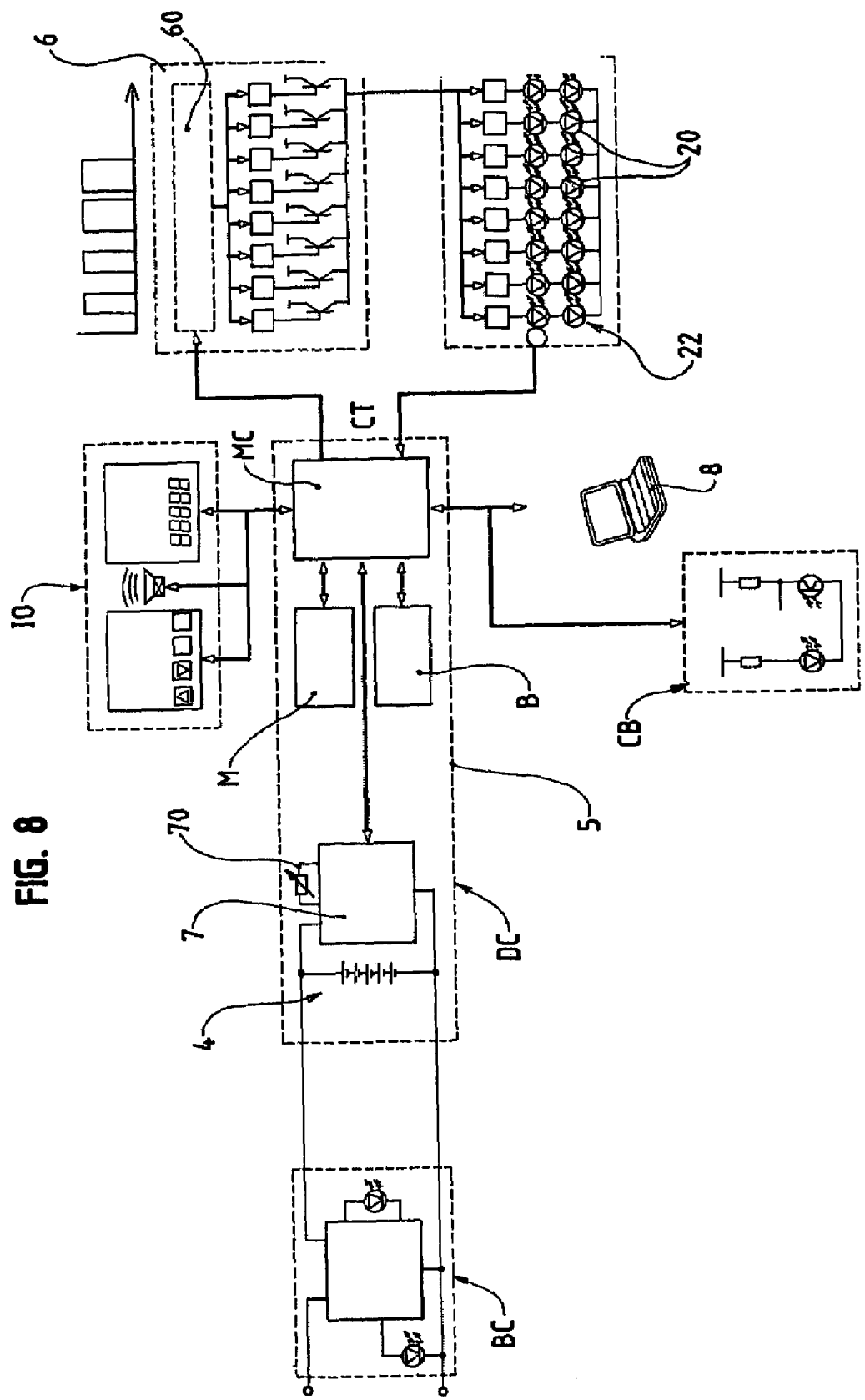
FIG. 8 is a more detailed plan of the electronic diagram of the device.

As for the LED diodes 20, they are preferably subdivided into elementary modules 22, as is schematically shown in FIG. 8, each comprising a number of LED diodes 20 which is identical or not, and supplied by regulation circuits. These latter make it possible, through the central unit 5, to supply the LED diodes 20 of each of these elementary modules 22 at well defined powers.

Furthermore, the energy source 4 is associated with a direct current/direct current converter device 7, commonly called a DC/DC converter, equipped with an adjustment potentiometer 70, and in the form of a module.

Figure 9:
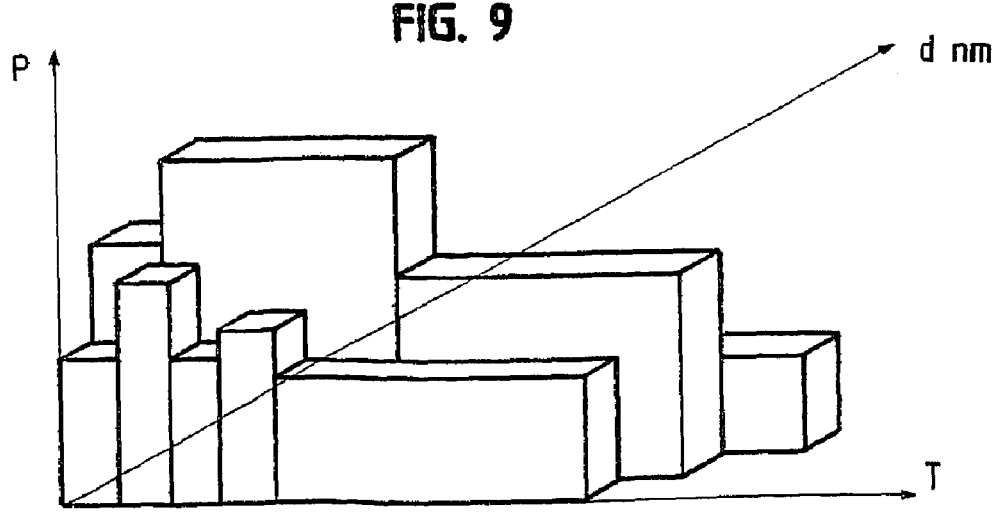
FIG. 9 is a graph illustrating the intensity or the density of illumination as a function of time, of the wave length and of the power of emission or of the number of emitting diodes.

As is more particularly visible in FIG. 9, the DC/DC module 7, just like a transformer in alternating mode, cuts the battery voltage and smoothes it in order to obtain a perfectly constant output voltage whatever the voltage issuing from the battery 4. An adjustment device makes it possible to adjust a basic output voltage which will then be modulated as a function of the information issuing from the temperature sensor.

Furthermore, the power card 6 comprises a circuit 60 for control by shift register and cyclic ratio modulation, making it possible to select and modulate the power of emission of each group of LEDs 20.

In order to optimize the integration of these elements in a portable, therefore not cumbersome, unit, the assembly of the shift registers and current regulation circuits may be grouped in an ASIC.

It should be noted in addition that the interest of this concept of shift registers and of regulation circuits for each module 22 of LED diodes 20, resides in the fact that it is not limited in terms of maximum luminosity, since a plurality of these modules 22 of LED diodes 20 may be placed in cascade.

In order to respond further to this preoccupation of integration, the ASIC may be mounted on the opposite face or the disc or discs 21 with respect to the LED diodes 20 or modules 22 of diodes.

FIG. 8 shows a diagram of the device in greater detail. The latter thus comprises in particular a charger unit BC, a direct current supply DC, a micro-controller MC connected to a memory M, to a library B and to an operator interface IO.

As shown in FIG. 8, the DC/DC module 7 is directly connected to the battery 4 of which it will lower the voltage to take it to the desired power reference value, this power reference being corrected in real time by the central unit card 5 as a function of the information issuing from a temperature sensor CT.

FIG. 8 graphically represents the supply power of each module 22 of LED diodes 20 for a determined energy profile, in the course of a defined radiation sequence. While FIG. 9 represents the intensity or the density of illumination as a function of time of the wave length and of the power of emission or of the number of emitting diodes.

This representation also makes it possible to demonstrate that, by using different cyclic ratios, the central unit 5 has the possibility of modulating the power of the LEDs therefore the power of the radiation emitted.

According to the invention, the device 1 thus comprises, in combination, means for adjusting one or more of the operating parameters of the light power, namely:

the intensity of illumination the cyclic ratio and/or the density of illumination per surface unit;

the monitoring of the temperature and/or duration of each of these sequences so as to adapt the polymerization energy profile as a function of the characteristics of the photo-polymerization lamp.

These means consist of means for selecting in a memory connected to said central unit 5, a determined energy profile from a plurality of profiles pre-recorded in this memory and/or a datum, there again, from a plurality having been previously recorded in said memory, relative to one or more of the adjustable parameters.

In this way, by way of example, in the DC/DC card 7, a chopping of the reference voltage will make it possible to vary the power of each group of diodes 20.

The operator may still have the choice, through a menu, between different pre-established energy powers. It should be noted that such selection means enable the operator to adjust this power.

A combination of these different types of adjustment means may, of course, be envisaged.

The device advantageously also comprises adjustment means, there again in the form of a potentiometer and/or of a touch screen and/or any other acquisition means, particularly remote ones, for the programmation of the memory connected to the central unit, precisely in order to record therein different energy values and/or different data relative to the adjustable parameters.

Figure 5:
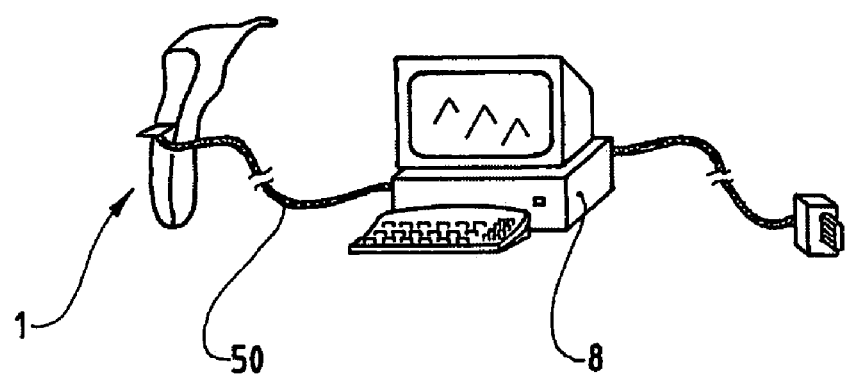
Figure 6:
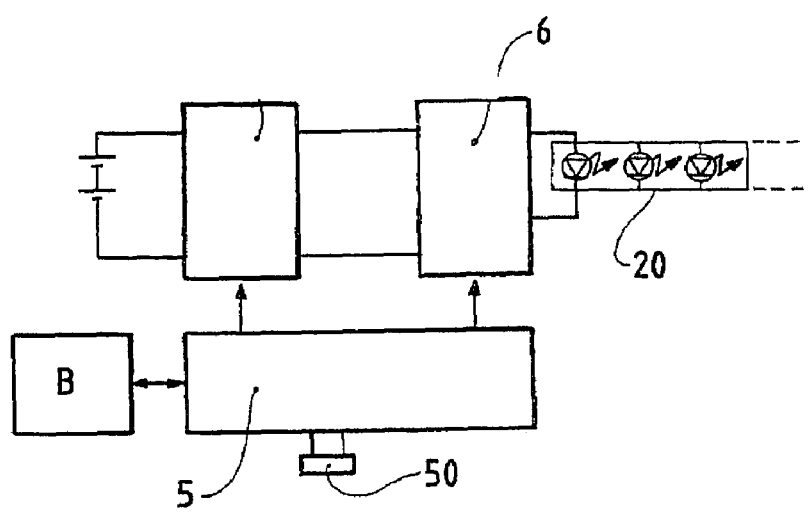
Figure 7:
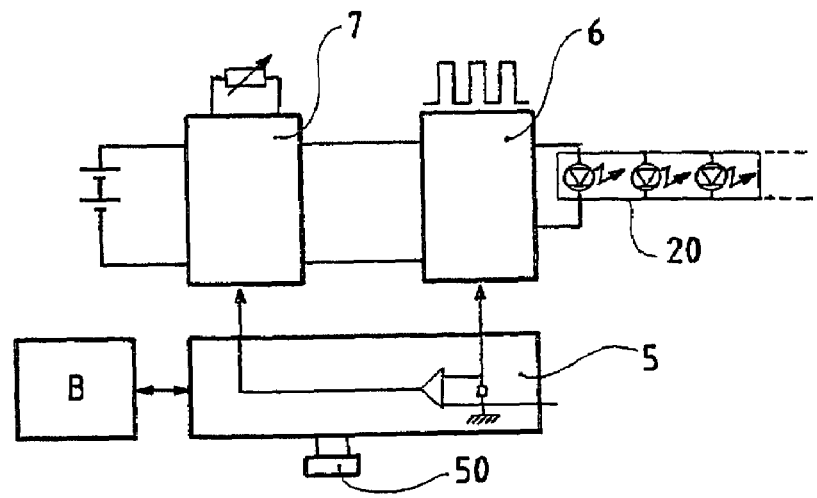

It should be noted that these adjustment means may employ means for downloading data, particularly through a micro-computer 8 via an RS232C interface 50, as shown in FIG. 5, in order to download, for example, new energy adjustments through a network of Internet type. These downloading means may also take the form of a modem, either directly integrated in the device, or in the loading support 11 to which reference has been made hereinabove in the description.

According to another form of embodiment, these power adjustment means may be in the form of bar code reading means CB.

It is also possible to use a memory in the form of a smart card, preferably of the programmable type, the device 1 comprising an appropriate reader. There again, this smart card reader may be found at the level of the loading support 11, in particular if it is desired to lighten the tool part that the user must manipulate.

Once again, it will be observed that the device 1 may comprise a combination of these different forms of embodiment of the acquisition means described hereinabove.

The particular purpose of the means for adjusting one or more of the parameters of the power of the light source is to intervene further on the density of illumination per surface unit, as indicated hereinabove. In effect, it is possible to adjust this density of illumination by intervening, particularly via the regulation circuits, on the number of LED diodes supplied at the level of each elementary module and/or on the intensity of their supply in the course of a photo-polymerization reaction.

It follows from the foregoing description that the present invention responds perfectly to the problem raised in that it brings a real response to the modification of power and to the thermal elevation of the LED lamps as present-day devices for the photo-polymerization of different types of composite materials. Taking everything into account, the device according to the invention gives the user the possibility of adjusting the operating conditions of his apparatus as he wishes, with the result that he is no longer limited, as was often the case in the past, to the use of a determined power and to a drop of this power in time.

The invention claimed is:

1. Electro-optical device for the photo-polymerization of composite materials, applicable in particular in the dental field, comprising:
  a light source (2) which is defined by an LED (20) or a group of LEDs,
  electronic power supply means comprising a battery (4) connected with a direct current/direct current converter device (7),
  passive means (3) for evacuation of heat, and
  a central management unit (5) for the operating parameters of the light source for the definition of a determined photo-polymerization energy profile, wherein,
  the direct current/direct current converter device (7) supplies control circuit by lowering the battery voltage, and
  the electronic power supply means comprises
    a circuit for control by shift register and cyclic ratio modulation to select and modulate the power of emission of each LED group,
    a direct polarization of the diodes by the output of the DC/DC converter by using the internal resistance of the diodes to provide a polarization voltage,
    a system for adjusting said polarization voltage in order to vary the supply current of the diodes and consequently the optical power, and
    an automatic correction of this polarization voltage by thermal servo-control in order to have available a constant output power.

2. Device according to claim 1, further comprising a power circuit to supply each LED (20) or group of LEDs (20) to a predefined value by cyclic ratio modulation.

3. Device according to claim 1, further comprising a device for correcting the thermal drift of the LEDs.

4. Device according to claim 2, further comprising a device for correcting the thermal drift of the LEDs.

5. Device according to claim 1, wherein the passive heat evacuation means comprises an LED supporting electronic card that includes metallic tracks for transfer of the heat from the base of each of the LEDs towards the periphery of the card.

6. Device according to claim 5, wherein the passive heat evacuation means further comprise a heat-conducting material disposed around each of the LEDs in order to remove the maximum of calories from each of the diodes and to transfer the removed calories to the periphery of the card.

7. Device according to claim 5, wherein the passive heat evacuation means further comprise a metallic radiator connected to the card by a heat-transmission paste or glue, and a thermal joint between said card and said radiator positioned towards a metal piece with high thermal inertia serving as receptacle for calories and as a support for the optical assemblies necessary for the system.

8. Device according to claim 7, wherein the passive heat evacuation means comprise a temperature sensor embedded in the thermal joint and making it possible to have, in real time, the temperature level of the optical assembly.

9. Device according to claim 5, wherein,
  the heat evacuation means further comprise one of the group consisting of:
    an electronic card on which the LEDs are welded, the welding spots being connected to electrical tracks, said electronic card is pierced with metallized thermal wells which conduct the calories as rapidly as possible towards the rear face of the card and therefore far from the LEDs,
    heat-conducting products placed in contact with peripheral walls of the diodes which are not in contact with the card itself, these products are pasty and deposited between the diodes then hardened thereafter, and
    a metallic radiator at the rear of the card, connected to said card by a paste or thermal glue, serving to recover the calories coming from the thermal wells traversing the card, wherein,
    all these elements are thermally connected by paste or thermal glue to a metallic piece of high thermal inertia which also serves as support for the optical elements, this latter piece serves to pump the calories rapidly and to store them temporarily when the lamp is lit and restores them more slowly by conduction or convection towards the assembly of the system when the lamp is not used, and further comprising
    a temperature detection system allowing the supply to be cut when the storage capacity of the metallic piece is attained.

10. Device according to claim 1, wherein the light source comprises a means for measuring the temperature adapted to detect the maximum storage of temperature compatible with the stability of optical power emitted.

11. Device according to claim 1, wherein the battery is of the Li ion battery type provided with a temperature sensor in order to securitize the apparatus.

12. Device according to claim 1, wherein the battery is a hybrid Ion battery and a charge level of the battery is displayed on an LCD screen.

13. Device according to claim 1, further comprising a potentiometer for readjustment of the power reference to adjust an industrial production to the same known value thanks to an individual adjustment of each apparatus.

14. Device according to claim 1, wherein the heat evacuation means comprise heat-conducting products placed in contact with peripheral walls of the diodes which are not in contact with the card itself, these products being solid and cut to the exact shape of the location of the diodes maintained intimately with the diodes by means of a heat conductor.

15. An electrooptical device for the photo-polymerization of composite materials, comprising:
- a light source (2) in the form of an optical cone and comprising electro-luminescent diodes (20);
- a support disc (21) extending perpendicularly to a longitudinal axis of the body (10) and supporting the diodes (20);
- a heat evacuation part (3) orienting and emitting heat energy produced by the light source (2) in a direction of a heat evacuation zone;
- an electronic power supply comprising a battery;
- a direct current/direct current converter device (7) connecting the battery to the light source (2);
- a central unit (5) managing operation of the light source (2) for definition of a determined photo-polymerization energy profile; and
- a device body (10) housing the light source, the energy source, the converter device, and the central unit, wherein,
- the direct current/direct current converter device (7) is configured to supply control circuit by lowering the battery voltage, and
- the electronic power supply comprises
  - a circuit for control by shift register and cyclic ratio modulation to select and modulate the power of emission of each LED group,
  - a direct polarization of the diodes by the output of the DC/DC converter by using the internal resistance of the diodes to provide a polarization voltage,
  - a system for adjusting said polarization voltage in order to vary the supply current of the diodes and consequently the optical power, and
  - an automatic correction of this polarization voltage by thermal servo-control in order to have available a constant output power.

16. The device of claim 15, further comprising:
a temperature sensor (CT), and wherein,
the converter device (7) is directly connected to the battery (4), the converter device lowering the voltage of the battery as a function of information issuing from the temperature sensor (CT).

17. The device of claim 15, wherein,
the determined photo-polymerization energy profiles are for activating photo initiators of dental composite materials.

18. An dental electro-optical device for the photo-polymerization of composite materials, comprising:
- a light source (2) comprising electro-luminescent diodes (20);
- a heat evacuation part (3) located to remove heat energy produced by the light source (2) in a direction of a heat evacuation zone;
- an electronic power supply comprising a battery;
- a direct current/direct current converter device (7) connecting a voltage of the battery to the light source (2);
- a central unit (5) managing operation of the light source (2) for definition of determined photo-polymerization energy profiles for activating photo initiators of dental composite materials;
- a power card (6) comprising a circuit (60) for power modulation, by shift register and cyclic ratio modulation, of emission of each diode; and
- a device body (10) housing the light source, the energy source, the converter device, the power card, and the central unit, wherein,
- the direct current/direct current converter device (7) is configured to supply control circuit by lowering the battery voltage, and
- the electronic power supply comprises
  - a circuit for control by shift register and cyclic ratio modulation to select and modulate the power of emission of each LED group,
  - a direct polarization of the diodes by the output of the DC/DC converter by using the internal resistance of the diodes to provide a polarization voltage,
  - a system for adjusting said polarization voltage in order to vary the supply current of the diodes and consequently the optical power, and
  - an automatic correction of this polarization voltage by thermal servo-control in order to have available a constant output power.

* * * * *